United States Patent [19]
Watkins

[11] Patent Number: 5,568,534
[45] Date of Patent: Oct. 22, 1996

[54] APPARATUS AND METHOD FOR SECURING, TRANSPORTING AND ANALYZING A SPECIMEN

[76] Inventor: Joseph T. Watkins, 38504 Shana Dr., Clinton Township, Macomb County, Mich. 48036

[21] Appl. No.: 272,687

[22] Filed: Jul. 8, 1994

[51] Int. Cl.$^6$ .................................................. H05G 1/00
[52] U.S. Cl. ........................................ 378/208; 378/210
[58] Field of Search ............................ 378/208, 209, 378/204, 210, 68, 64; 356/244; 250/453.11

[56] References Cited

U.S. PATENT DOCUMENTS

| | | | |
|---|---|---|---|
| 328,995 | 10/1885 | Andrews | 269/54.5 |
| 1,462,717 | 7/1923 | Maus | 269/293 |
| 2,464,114 | 3/1949 | Bloecher | 269/54.5 |
| 2,599,681 | 6/1952 | Wells | 269/54.5 |
| 3,433,105 | 3/1969 | Barickman | 269/54.5 |
| 3,817,138 | 6/1974 | Lasker | 83/466.1 |
| 4,056,026 | 11/1977 | Panaritis et al. | 83/454 |
| 4,890,525 | 1/1990 | Bilbao | 83/761 |
| 4,934,026 | 6/1990 | McNerney | 83/762 |
| 4,974,291 | 12/1990 | McNerney | 83/762 |
| 4,993,056 | 2/1991 | Lary | 378/208 |
| 5,002,735 | 3/1991 | Alberhasky et al. | 378/208 |
| 5,020,088 | 5/1991 | Tobin | 378/208 |

*Primary Examiner*—Don Wong
*Attorney, Agent, or Firm*—Young & Basile, P.C.

[57] ABSTRACT

An apparatus for orienting, securing and analyzing a specimen comprises a base for receiving the specimen. A cover is receivable over the specimen and base, and an adjustable mechanism is provided for securing the cover to the base. The apparatus further comprises a mechanism, disposed on at least one of the base and cover, for identifying a discrete, localized area on the specimen. A method for securing and analyzing a specimen, wherein a radiation is used to analyze the specimen, comprises the steps of: placing the specimen on a base; securing a cover having radiation-evident coordinate indicia thereon over the specimen and the base so as to snugly engage the specimen between the cover and the base, the cover being formed from a material transparent to the radiation and comprising a plurality of openings adapted to receive a tool for cutting the specimen; irradiating the specimen so as to produce a diagnostic medium having the specimen irradiation results and the radiation-evident coordinate indicia thereon; identifying any medically suspect areas in the specimen via the coordinate indicia; and cutting specimen samples of the suspect areas through the openings located adjacent the suspect areas.

21 Claims, 3 Drawing Sheets

APPARATUS AND METHOD FOR SECURING, TRANSPORTING AND ANALYZING A SPECIMEN

BACKGROUND OF THE INVENTION

The present invention relates generally to an apparatus for securing a specimen, and more particularly to such an apparatus able to secure, transport and house the specimen during subsequent diagnostic irradiation and preparation of tissue samples.

Currently, when a biopsy is taken from a body, for example, from a woman's breast to make a cancer diagnosis, the specimen is merely put in a jar or other like container. It is quite difficult to insure that the proper orientation is kept, ie. medial, lateral, posterior, nipple, when the specimen is taken out of the container to be irradiated by, for example, an X-ray. Further, it is quite difficult for the doctor/radiologist to precisely identify for the pathologist or technician the medically suspect areas within the specimen. Still further, even if the suspect areas were identified accurately, there is yet the possibility that the pathologist or technician may prepare tissue samples taken from the wrong areas. As such, there is a fair amount of guesswork, even for the most skilled doctors and pathologists, involved in the current procedure for evaluation and diagnosis of biopsy specimens. As can be appreciated, any error created due to the uncertainties outlined above may result in misdiagnosis of a particular sample, which may have unfortunate or even disastrous consequences.

Thus, it is an object of the present invention to provide an apparatus and method for securing, transporting and analyzing a specimen, which apparatus advantageously houses the specimen from the moment it is taken from the patient's body until the time the tissue samples are prepared from it. It is a further object of the present invention to provide such an apparatus which is sufficiently transparent to the diagnostic radiation used so as to prevent undesirable interference with the testing medium. Still further, it is an object of the present invention to provide such an apparatus which will provide resistance from the specimen rotating from its initial orientation as placed within the apparatus by the surgeon. Yet still further, it is an object of the present invention to provide such an apparatus which is size adjustable so as to closely fit variously sized specimens. Still further, it is an object of the present invention to provide such an apparatus having means for precisely identifying any suspect areas in the specimen, which means may be used by the radiologist as well as the pathologist cutting and preparing the tissue samples from the specimen. Yet still further, it is an object of the present invention to provide such an apparatus and method which is cost effective and saves a large amount of time and expense in cutting and preparing tissue samples.

SUMMARY OF THE INVENTION

The present invention addresses and solves the above-mentioned problems by providing an apparatus for securing and analyzing a specimen, the apparatus comprising a base for receiving the specimen. A cover is receivable over the specimen and base, and adjustable means are provided for securing the cover to the base. The apparatus further comprises means, disposed on at least one of the base and cover, for identifying a discrete, localized area on the specimen.

A method for securing and analyzing a specimen, wherein a radiation is used to analyze the specimen, comprises the steps of: placing the specimen on a base; securing a cover having radiation-evident coordinate indicia thereon over the specimen and the base so as to snugly engage the specimen between the cover and the base, the cover being formed from a material transparent to the radiation and comprising a plurality of openings adapted to receive a tool for cutting the specimen, the openings being oriented in order to reduce any undesirable radiation diffraction; irradiating the specimen so as to produce a diagnostic medium having the specimen irradiation results and the radiation-evident coordinate indicia thereon; identifying any medically suspect areas in the specimen via the coordinate indicia; and cutting specimen samples of the suspect areas through the openings located adjacent the suspect areas.

BRIEF DESCRIPTION OF THE DRAWINGS

Other objects, features and advantages of the present invention will become apparent by reference to the following detailed description and to the drawings, in which.

DETAILED DESCRIPTION OF THE PREFERRED EMBODIMENTS

Figure 1:
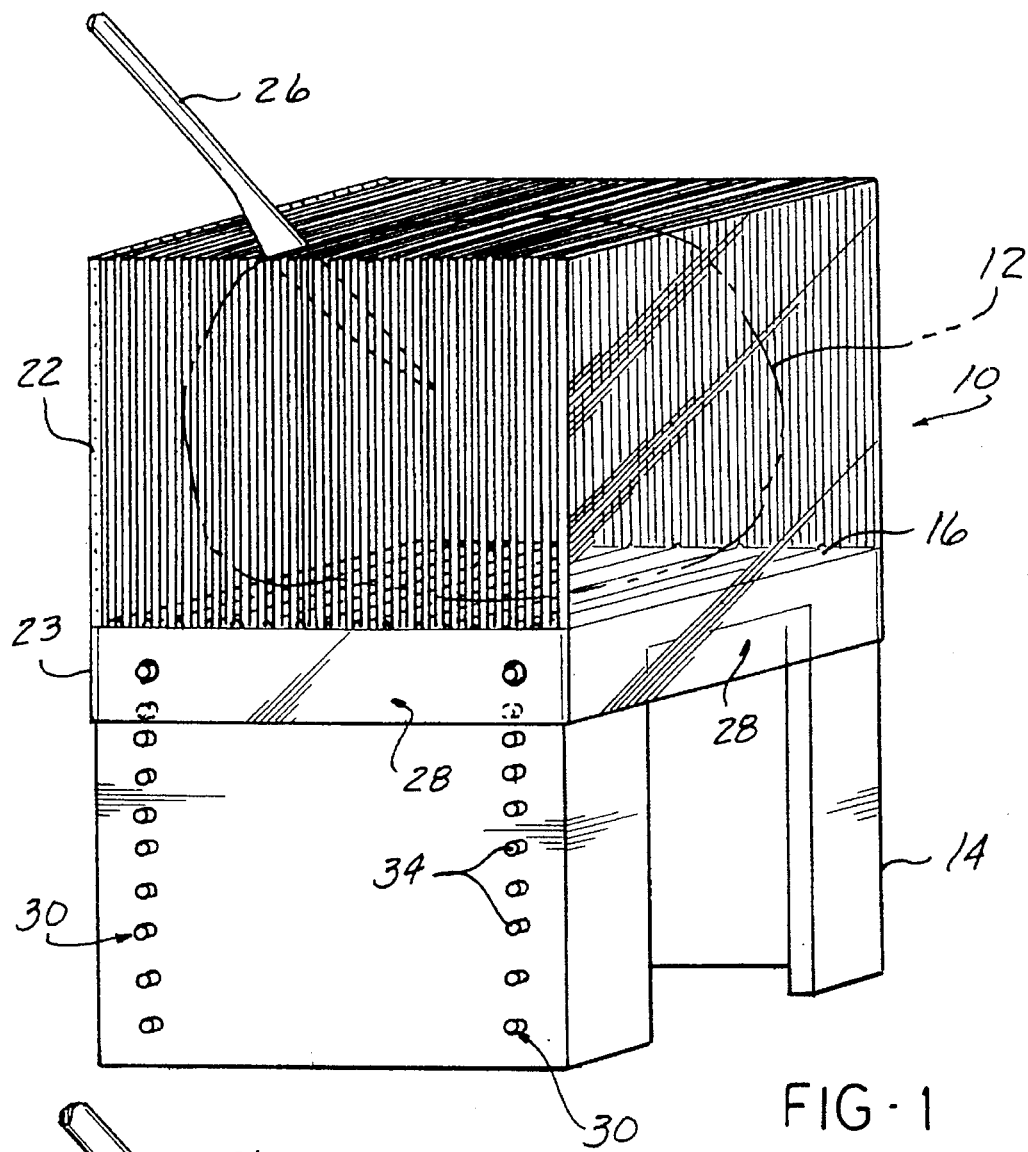
FIG. 1 is a perspective view of the apparatus of the present invention, showing a specimen in phantom therein, and a scalpel cutting into the specimen.
Figure 2:
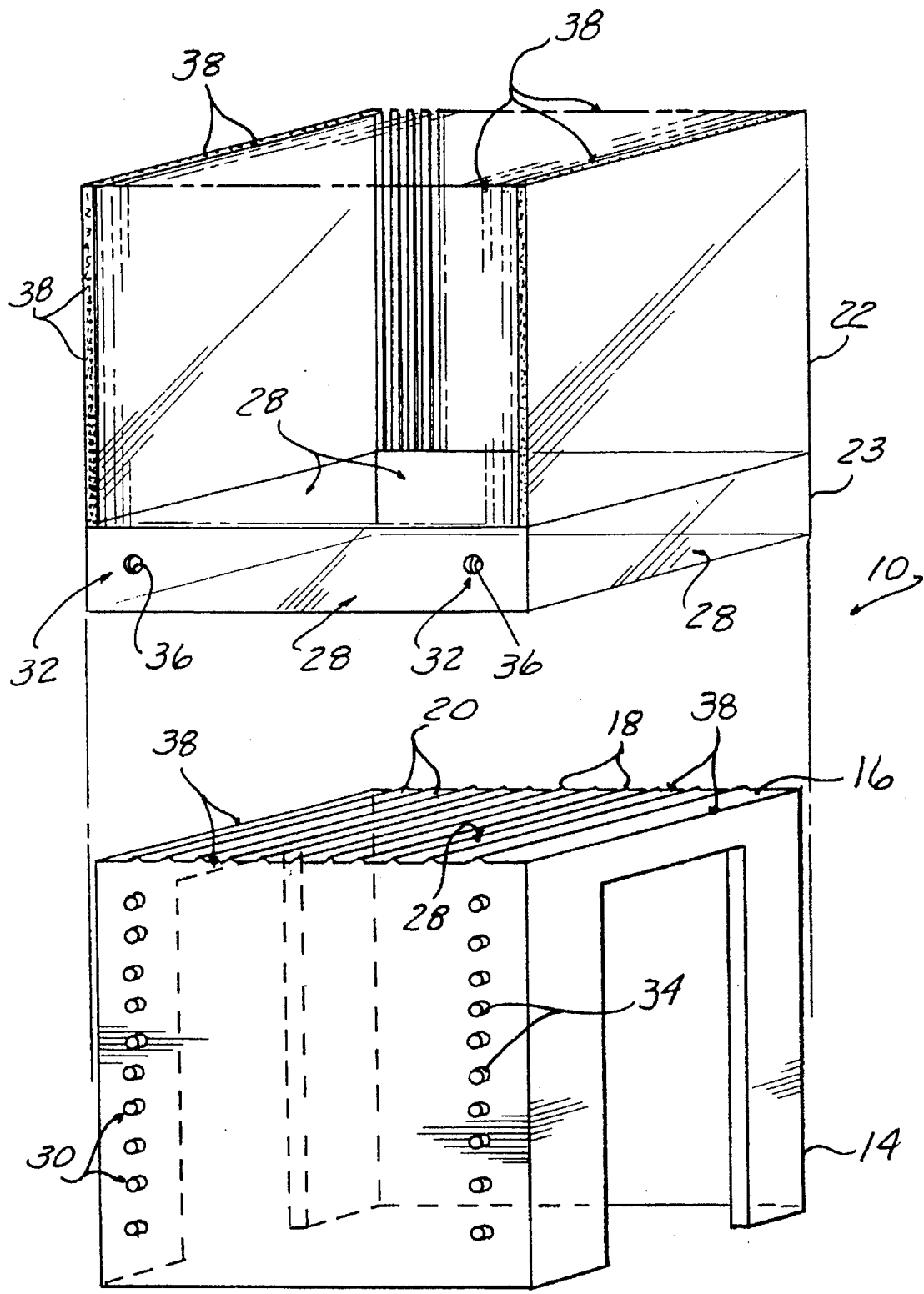
FIG. 2 is an exploded perspective view of the apparatus of the present invention.

Referring now to FIG. 1, the apparatus of the present invention for securing and analyzing a specimen 12 is designated generally as 10. Apparatus 10 comprises a base 14 for receiving the specimen 12. It is to be understood that base 14 may be made of any suitable material and shape in accord with the present invention. However, in the preferred embodiment, base 14 is made of a suitably rigid, slightly flexible polymeric material, and has a substantially inverted U-shape, as best seen in FIGS. 1 and 2. The base 14 is slightly rigid so as to be able to mildly flex in response to selectively applied pressure in the direction of the arrows in FIG. 2.

Figure 4:
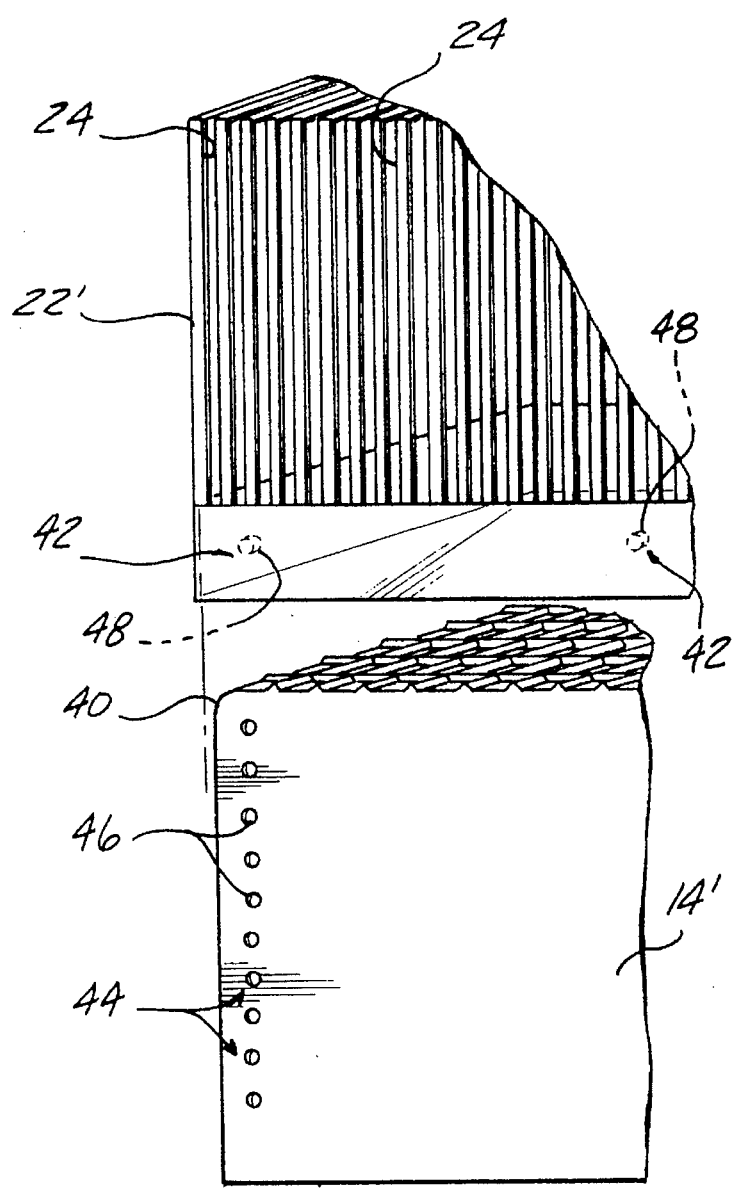
FIG. 4 is a cutaway, exploded perspective view of a further embodiment of the present invention, showing an alternate configuration of the specimen rotation-resistant recesses and ridges, as well as the inwardly extending male projections and the downwardly extending female portions.

Base 14 has an upper, specimen contacting surface 16. Base 14 may further comprise means for providing resistance to specimen 12 rotation. This is an important part of the present invention, in order to insure that the specimen remains oriented in the position it was removed from the body, in order to provide accurate analysis and diagnosis. It is to be understood that this resistance providing means may comprise any suitable means, however, in a preferred embodiment, this means comprises a plurality of ridges 18 having recesses 20 therebetween, as best seen in FIGS. 2 and 4. The recesses 20 are adapted to receive an adjacent portion of the specimen 12, and the ridges 18 slightly impress into specimen 12. This aids in preventing specimen 12 from rotating in any direction.

Figure 5:
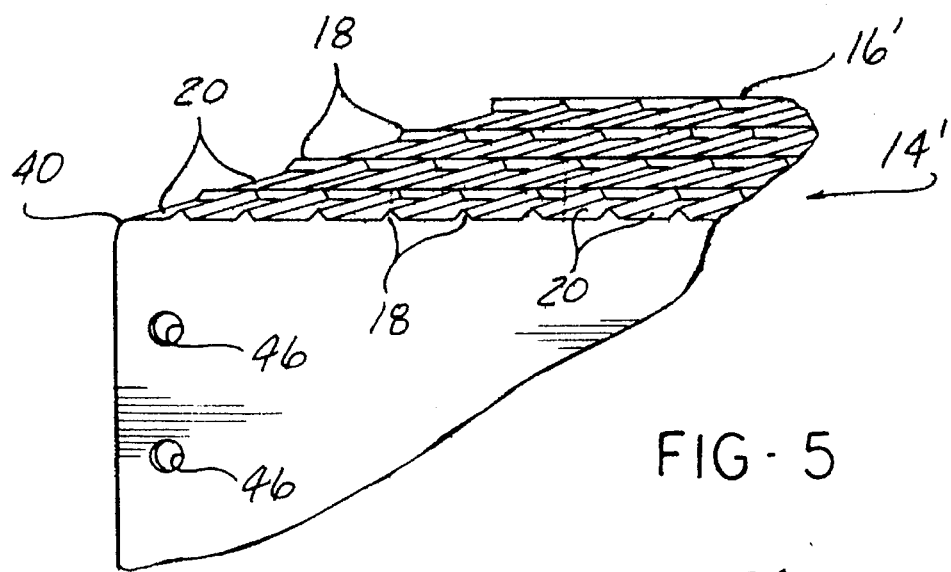
FIG. 5 is an enlarged, cutaway perspective view of the base of FIG. 4, showing the recesses and ridges, as well as two female portions.

In a more preferred embodiment, as best seen in FIG. 5, the base 14' has an upper, specimen contacting surface 16' having curved edges 40. The ridges 18 extend both longitudinally and transversely; as do the recesses 20, thereby forming a criss-cross pattern. This configuration may give further aid in preventing specimen 12 from rotating in any direction.

As is generally known in the art, a radiation is used to analyze the specimen 12. It is to be understood that the present invention is useful for any such type of radiation typically used in diagnostic testing, for example, but not limited to, X-ray analysis, magnetic resonance imaging (MRI), CT scanning, ultrasound imaging, and the like.

Figure 3:
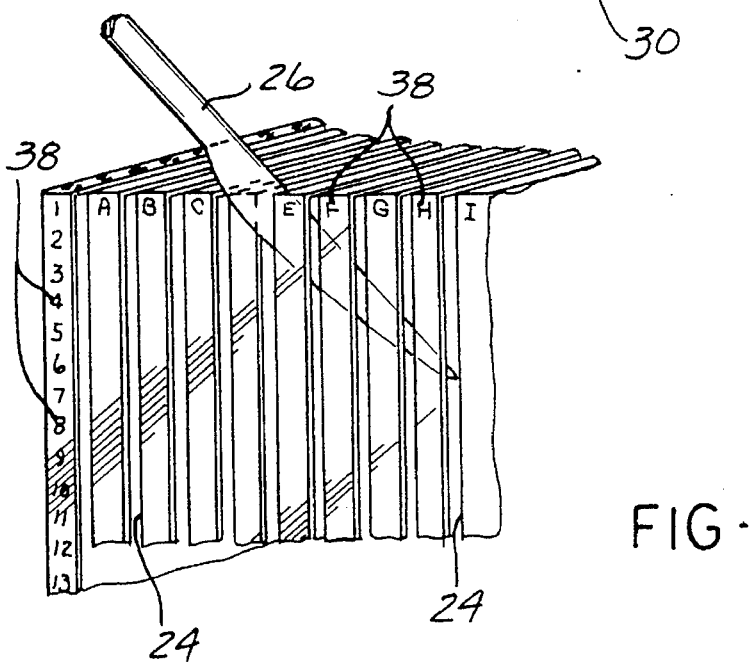
FIG. 3 is an enlarged, cutaway perspective view showing the radiation-evident coordinate indicia of the present invention.

Referring now to FIG. 3, a cover 22 is receivable over the specimen 12 and base 14. Cover 22 is formed from a suitably rigid, slightly flexible polymeric material, which is transparent to the radiation used in the diagnostic testing, the cover 22 comprising a plurality of openings 24 adapted to receive a tool 26 for cutting the specimen 12. It is to be understood that any suitable tool 26 or machine may be used for cutting tissue samples. For example, lasers and the like may be used. As shown in FIGS. 1 and 3, a scalpel is used.

It is to be further understood that openings 24 may be of any suitable size and shape, and may be oriented in order to reduce undesirable radiation diffraction (if any). The presence of such undesirable diffraction may result in misdiagnosis of the specimen contained within apparatus 10. In the preferred embodiment, the base 14 has a length of about 10 cm, a width of about 10 cm, and a height of about 10.5 cm. Cover 22 has a length of approximately 10 cm, a width of approximately 10 cm, and a height of approximately 10.2 cm. The openings are substantially in the form of longitudinal slits about 1 mm wide, which extend from the front to the back of cover 22, and from the top of cover 22 to the upper, specimen contacting surface 16, as best seen in FIGS. 1 and 3. However, it is to be understood that these sizes are merely exemplary, and any suitable size and shape may be used, as desired for a particular application and/or specimen size.

The apparatus 10 may further comprise at least one area 28 for labelling the specimen 12, the labelling area 28 situated such that it does not interfere with analyzing of the specimen 12. It is to be understood that this labelling area 28 may comprise any suitable size, shape, orientation and location. It is contemplated that the labelling area 28 may be disposed on the upper, specimen contacting surface 16. However, in the preferred embodiment, the cover 22 has a base contacting portion 23 extendable below the specimen contacting surface 16, as best seen in FIG. 1. The labelling area 28 is defined in the base contacting portion 23. This area 28 may be used to specify any needed patient information, as well as the orientation of the specimen. For example, when the apparatus 10 is used to secure and analyze a breast tissue specimen, the labelling areas 28 on each of the four sides (as depicted; it is to be understood that any number of sides or shapes may be incorporated as desired in the present invention) may be, for example, "Medial", "Lateral", "Nipple" and "Posterior".

The apparatus 10 of the present invention further comprises adjustable means for securing the cover 22 to the base 14. It is to be understood that this means may comprise any suitable means. However, in a preferred embodiment, as best seen in FIGS. 1 and 2, this means comprises mating, selectively engageable coupling members. One coupling member 30 is disposed on the base 14, and the other coupling member 32 is disposed on the cover 22. It is to be further understood that these coupling members 30, 32 may be of any suitable size and shape. In the preferred embodiment, coupling member 30 comprises at least one male projection 34, and the other coupling member 32 comprises a female portion or throughbore 36 complementarily shaped to the male projection 34.

Still more preferred are a plurality of male projections 34 extending in a downward direction from the specimen contacting surface 16, the projections 34 oriented such that the female portion 36 may selectively be coupled with one male projection 34 in order to provide snug contact between the specimen 12 and the cover 22. In FIG. 1, this snug contact is provided by coupling the uppermost male projections 34 with the corresponding female portions 36.

In this preferred embodiment, the projections 34 are selectively snap fit into female portions 36 by applying a slight amount of force or pressure in the direction of the arrows in FIG. 2 in order to remove projections 34 from female portions 36, thereby freely moving cover 22 in an upward or downward direction over base 14. When the force is removed, the projections 34 will "snap" into the closest female portions 36.

In a more preferred embodiment, as best seen in FIGS. 4 and 5, this adjustable securing means comprises mating, selectively engageable coupling members. One coupling member 42 is disposed on the cover 22' and the other coupling member 44 is disposed on the base 14'. It is to be further understood that these coupling members 42, 44 may be of any suitable size and shape. In the preferred embodiment, the other coupling member 44 comprises at least one female portion or indentation 46, and the one coupling member 42 comprises an inwardly extending male projection 48. The female portion 46 is complementarily shaped to the male projection 42.

Still more preferred are a plurality of female portions 46 extending in a downward direction from the specimen contacting surface 16', the portions 46 oriented such that the male projection 42 may selectively be coupled with one female portion 46 in order to provide snug contact between the specimen 12 and the cover 22'. Each of the female portions or indentations 46 is complementarily shaped to the male projection 42.

It is to be further understood that any of the coupling members discussed above may be located on the front of the apparatus (as depicted in the Figures), and/or on the back and/or on the sides of the apparatus.

The apparatus 10 may further comprise means, disposed on at least one of the base 14 and cover 22, for identifying a discrete, localized area on the specimen 12. It is to be understood that this means may comprise any suitable means. However, in the preferred embodiment, this identifying means comprises radiation-evident coordinate indicia 38. These indicia 38 may be of any suitable form, however, in the preferred embodiment, as best seen in FIG. 3, the x-coordinate is a series of letters, and the y-coordinate is a series of numbers. For example, a radiologist may identify a suspect area as being located at "G-8". Since these indicia are radiation-evident, they will be projected onto the diagnostic medium, such as an X-ray or CT scan. It is to be understood that the indicia may be made from any suitable material to insure that they are visible light evident and/or radiation evident. For example, if used in X-ray analysis, it may be desired to have the indicia 38, in addition to being visible light evident, formed from a radio opaque material, such as a suitable lead-based material.

It is to be further understood that the indicia 38 may be placed in any suitable location on the apparatus 10, however, in the preferred embodiment, the coordinate indicia 38 are disposed on the cover 22, preferably on the front and top sides (as shown in FIGS. 2 and 3), as well as on the back side of cover 22. In order to aid the pathologist or lab technician who will be preparing the tissue samples subsequent to the radiologist examining the diagnostic medium, it is preferred that the coordinate indicia 38 are visible light-evident also. In that way, with the specimen 12 still within apparatus 10, the pathologist may make the incision into the specimen through the openings 24 located adjacent, for example, "G-8".

A method according to the present invention comprises the steps of:

placing the specimen 12 on a base 14;

securing a cover 22 having radiation-evident coordinate indicia 38 thereon over the specimen 12 and the base 14 so as to snugly engage the specimen 12 between the cover 22 and the base 14 (as seen in FIG. 1);

irradiating the specimen 12 so as to produce a diagnostic medium (not shown), such as an X-ray, CT scan, and the like, the medium having the specimen irradiation results and the radiation-evident coordinate indicia 38 projected thereon;

identifying any medically suspect areas in the specimen 12 via the coordinate indicia 38; and cutting specimen samples of the suspect areas through the openings 24 located adjacent the suspect areas.

This method is advantageous in that the specimen 12 will remain oriented as taken from the body, the radiologist will be able to ascertain suspect areas from the diagnostic medium, and with great accuracy due to the coordinate indicia 38, will be able to direct the pathologist preparing the tissue samples substantially precisely to the area in which to make the tissue incisions. The present invention is also advantageous in that, due to its design and the materials used, it may be made quite inexpensively and quickly. This is desirable, in that the apparatus, due to medical procedure and disease control, in some cases should be sterile. In that situation, the apparatus is usually used only a single time, after which it may be discarded.

Some of the more important advantages of the present invention include the following. The apparatus and method provide a means of easy specimen orientation for the surgeon. The radiologist has a means of simply and substantially precisely locating suspect areas. The pathologist, due to the substantially precise location of the suspect areas, may prepare a significantly fewer number of specimen tissue slides, thereby saving a great deal of time and money, both for the hospital and the patient.

While preferred embodiments of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. An apparatus for securing and analyzing a specimen, wherein a radiation is used to analyze the specimen and reveal a medically suspect area, the apparatus comprising:

a base for receiving the specimen;

a cover having a front and a back, and formed from a material transparent to the radiation and receivable over the specimen and base;

a plurality of longitudinal slits defined in the cover, the slits extending from the front to the back of the cover, the slits adapted to receive a tool for slicing a tissue sample of the medically suspect area from the specimen while within the apparatus;

adjustable means, adapted to closely fit variously sized specimens, for securing the cover to the base; and means, disposed on at least one of the base and cover, for identifying a discrete, localized area on the specimen, each of the plurality of slits located substantially adjacent the identifying means.

2. The apparatus as defined in claim 1, wherein the base comprises means for providing resistance to specimen rotation.

3. The apparatus as defined in claim 2 wherein the base has an upper, specimen contacting surface and wherein the resistance providing means comprises a plurality of ridges having recesses therebetween, the recesses being adapted to receive an adjacent portion of the specimen.

4. The apparatus as defined in claim 1 wherein the identifying means comprises visible light-evident coordinate indicia.

5. The apparatus as defined in claim 1, further comprising at least one area for labelling the specimen, the labelling area situated such that it does not interfere with analyzing of the specimen.

6. The apparatus as defined in claim 5 wherein the base has an upper, specimen contacting surface, the cover has a base contacting portion extendable below the specimen contacting surface, and the labelling area is defined in the base contacting portion.

7. The apparatus as defined in claim 1 wherein the adjustable means comprises mating, selectively engageable coupling members, one coupling member disposed on the cover, and the other coupling member disposed on the base.

8. The apparatus as defined in claim 7 wherein the one coupling member comprises at least one male projection, and the other coupling member comprises a female portion complementarily shaped to the male projection.

9. The apparatus as defined in claim 8 wherein the base has an upper, specimen contacting surface, and wherein there are a plurality of female portions extending in a downward direction from the specimen contacting surface, the portions oriented such that the male projection may selectively be coupled with one female portion in order to provide snug contact between the specimen and the cover.

10. The apparatus as defined in claim 1 wherein a radiation is used to analyze the specimen, and the identifying means comprises radiation-evident coordinate indicia.

11. The apparatus as defined in claim 10 wherein the coordinate indicia are disposed on at least one of the cover and the base.

12. An apparatus for securing and analyzing a specimen, wherein a radiation is used to analyze the specimen and reveal a medically suspect area, the apparatus comprising:

a base for receiving the specimen, the base having an upper, specimen contacting surface and comprising means for providing resistance to specimen rotation, wherein the resistance providing means comprises a plurality of ridges having recesses therebetween, the recesses being adapted to receive an adjacent portion of the specimen;

a cover having a front and a back, and formed from a material transparent to the radiation and receivable over the specimen and base;

a plurality of longitudinal slits defined in the cover, the slits extending from the front to the back of the cover, the slits adapted to receive a tool for slicing a tissue sample of the medically suspect area from the specimen while within the apparatus, the slits being oriented in order to reduce any undesirable radiation diffraction;

adjustable means, adapted to closely fit variously sized specimens, for securing the cover to the base, wherein the adjustable means comprises mating, selectively engageable coupling members, one coupling member disposed on the cover, and the other coupling member disposed on the base;

means, disposed on at least one of the base and cover, for identifying a discrete, localized area on the specimen, wherein the identifying means comprises visible light-evident coordinate indicia, each of the plurality of slits located substantially adjacent the coordinate indicia; and at least one area for labelling the specimen, the labelling area situated such that it does not interfere with analyzing of the specimen.

13. The apparatus as defined in claim 12 wherein the cover has a base contacting portion extendable below the specimen contacting surface, and the labelling area is defined in the base contacting portion.

14. The apparatus as defined in claim 12 wherein the one coupling member comprises a male projection, and the other coupling member comprises a plurality of female portions, each female portion complementarily shaped to the male projection, wherein the female portions extend in a downward direction from the specimen contacting surface, the portions oriented such that the male projection may selectively be coupled with one female portion in order to provide snug contact between the specimen and the cover.

15. The apparatus as defined in claim 12 wherein the coordinate indicia are disposed on the cover, and wherein the coordinate indicia are radiation-evident.

16. A method for securing and analyzing a specimen, wherein a radiation is used to analyze the specimen and reveal a medically suspect area, the method comprising the steps of:

placing the specimen on a base;

securing a cover having visible light-evident coordinate indicia thereon over the specimen and the base so as to snugly engage one of variously sized specimens between the cover and the base, the cover having a front and a back, and being formed from a material transparent to the radiation and comprising a plurality of longitudinal slits extending from the front to the back of the cover, the slits adapted to receive a tool for slicing a tissue sample of the medically suspect area from the one specimen while engaged between the cover and the base, each of the plurality of slits located substantially adjacent the coordinate indicia;

irradiating the specimen so as to produce a diagnostic medium having the specimen irradiation results thereon;

identifying the medically suspect area in the specimen via the coordinate indicia; and cutting the tissue sample of the suspect area through the slits located adjacent the suspect area.

17. The method as defined in claim 16 wherein the base has an upper, specimen contacting surface comprising a plurality of ridges having recesses therebetween, the recesses being adapted to receive an adjacent portion of the specimen, for providing resistance to specimen rotation.

18. The method as defined in claim 16 wherein at least one male projection is defined in one of the base and the cover, and a female portion complementarily shaped to the male projection is defined in the other of the base and cover, for selectively securing the cover to the base.

19. The method as defined in claim 18 wherein the base has an upper, specimen contacting surface, and wherein there are a plurality of female portions disposed on the base and extending in a downward direction from the specimen contacting surface, the portions oriented such that the male projection defined in the cover may selectively be coupled with one female portion in order to provide snug contact between the specimen and the cover.

20. A method for securing and analyzing a specimen, wherein a radiation is used to analyze the specimen and reveal a medically suspect area, the method comprising the step of:

irradiating one of variously sized specimens so as to produce a diagnostic medium having the specimen irradiation results and radiation-evident coordinate indicia thereon, the one specimen located between a cover and a base, the cover having the radiation-evident coordinate indicia thereon, the cover having a front and a back, and formed from a material transparent to the radiation and comprising a plurality of longitudinal slits extending from the front to the back of the cover, the slits adapted to receive a tool for slicing a tissue sample of the medically suspect area from the specimen while located between the cover and the base, each of the plurality of slits located substantially adjacent the coordinate indicia, the slits being oriented in order to reduce any undesirable radiation diffraction.

21. The method as defined in claim 20, further comprising the steps of:

identifying the medically suspect area in the one specimen via the coordinate indicia; and slicing the tissue sample of the suspect area through the slits located adjacent the suspect area.

* * * * *